(12) United States Patent
Smith

(10) Patent No.: US 9,915,616 B2
(45) Date of Patent: Mar. 13, 2018

(54) METHOD TO IDENTIFY CHEMICAL COMPOUNDS USING COLORIMETRIC SPOT TESTS

(71) Applicant: FGROUPIP1, LLC, Washington, DC (US)

(72) Inventor: Eugene T. Smith, Jupiter, FL (US)

(73) Assignee: FGROUPIP1, LLC, Washington, DC (US)

( * ) Notice: Subject to any disclaimer, the term of this patent is extended or adjusted under 35 U.S.C. 154(b) by 1120 days.

(21) Appl. No.: 13/938,944

(22) Filed: Jul. 10, 2013

(65) Prior Publication Data

US 2014/0017802 A1    Jan. 16, 2014

Related U.S. Application Data

(60) Provisional application No. 61/669,945, filed on Jul. 10, 2012.

(51) Int. Cl.
*G01N 31/22* (2006.01)
*G01N 21/78* (2006.01)
*G01N 31/00* (2006.01)

(52) U.S. Cl.
CPC ............. *G01N 21/78* (2013.01); *G01N 31/22* (2013.01)

(58) Field of Classification Search
CPC ........ G01N 21/03; G01N 21/00; G01N 21/78; G01N 21/77; B01L 2400/0406; B01L 2400/0403; B01L 2400/04; B01L 2400/00
USPC .................................................. 436/165, 164
See application file for complete search history.

(56) References Cited

U.S. PATENT DOCUMENTS

| | | | |
|---|---|---|---|
| 4,104,027 A | 8/1978 | Carroll | |
| 4,806,487 A | 2/1989 | Akers et al. | |
| 5,182,707 A * | 1/1993 | Cooper | G06F 15/025 422/404 |
| 7,267,799 B1 * | 9/2007 | Borich | G01N 21/8483 235/462.11 |
| 7,968,062 B1 | 6/2011 | Putnam | |
| 2002/0021828 A1 | 2/2002 | Papier et al. | |
| 2003/0021454 A1 | 1/2003 | Weyl | |
| 2003/0053085 A1 | 3/2003 | Takemoto | |
| 2004/0151624 A1 | 8/2004 | Erdman et al. | |
| 2005/0130312 A1 | 6/2005 | Glattstein | |
| 2008/0274014 A1 * | 11/2008 | Jumonville | A61B 10/007 422/400 |
| 2009/0280574 A1 | 11/2009 | Bryant | |
| 2010/0067030 A1 | 3/2010 | Imai et al. | |
| 2010/0232688 A1 | 9/2010 | Komiya et al. | |
| 2011/0117664 A1 | 5/2011 | Amisar | |
| 2012/0008004 A1 | 1/2012 | Kerby | |
| 2012/0045842 A1 * | 2/2012 | Petrich | G01N 33/48764 436/95 |

FOREIGN PATENT DOCUMENTS

| | | | |
|---|---|---|---|
| EP | 2 151 686 A1 * | 2/2010 | .......... G01N 33/487 |
| WO | 2010021873 | 2/2010 | |
| WO | 2012131386 | 10/2012 | |

OTHER PUBLICATIONS

"Color test reagents/ kits for preliminary identification of drugs of abuse", National Institute of Justice (2000): NIJ Standard 0604.01. (26 pages).
"False positives", AskDocWeb (2013). Retrieved on Nov. 20, 2013 from http://www.askdocweb.com/falsepositives.html (28 pages).
Niederwieser et al., "Glycolic acid in urine. A colorimetric method with values in normal adult controls and in patients with primary hyperoxaluria", Clinica Chimica Acta (1978) 89: 13-23.
Hasan et al., "Using laboratory chemicals to imitate illicit drugs in a forensic chemistry activity", J Chem Ed (2008) 85: 813-816.
Lampe, "Qualitative identification of narcotics by spot test examination", J Chem Ed (1958) 35: 96-97.
Masoud, "Systematic identification of drugs of abuse I: Spot tests", J Pharm Sci (1975) 64: 841-844.
O'Neal et al., "Validation of twelve chemical spot tests for the detection of drugs of abuse", Forensic Sci International (2000) 109: 189-201.
Pin et al., "Presumptive testing of amphetamine-type stimulants via colour tests", AJSTD (2010) 27(1): 66-75.
Rouse et al., "Presumptive & confirmatory drug tests using analogs of illicit drugs" Florida Atlantic University (2012). (poster).

* cited by examiner

*Primary Examiner* — Christine T Mui
(74) *Attorney, Agent, or Firm* — Fox Rothschild LLP

(57) ABSTRACT

A method to identify a compound of interest includes the step of subjecting a sample to a plurality of colorimetric spot tests to yield a plurality of resultant test colors. The resultant test colors are compared with reference colors to define a set of sample reference colors. Indexed reference color sets indexed for the compound of interest are provided. The indexed reference color sets are searched with one or more of the sample reference colors for a match with the set of sample reference colors. The identity of the sample as the compound of interest is then determined. A device and a system to identify compounds of interest are also disclosed.

12 Claims, 5 Drawing Sheets

| Sample | Chen 5 | Chromo 15 | Cobalt 17 | FeCl₃ 19 | Froehdes 24 | Marquis 7 | Meckes 4 | Nitric 1 | Simons 9 |
|---|---|---|---|---|---|---|---|---|---|
| Aceto-minophen | 3 5 | 19 | 19 17 3 5 | 21 23 | 6 3 15 | 19 15 | 19 12 16 | 15 1 | |
| Chloroaceto-phenone | 3 5 | 12 16 | 19 17 | 15 | | 16 | 16 12 | 19 | 3 5 18 19 |
| Chlor-promazine | 3 5 | 15 17 | 16 3 | 16 | 12 15 | 17 | 24 10 4 | 12 | 15 |
| Diphen-hydramine | 5 | 12 | 3 | 16 19 | 16 12 16 | 7 12 | 16 12 | 19 | 2 |
| Glycolate | 3 5 | 3 5 10 | 19 17 | 16 | 19 | 19 | 19 | 19 | 15 |
| Indole | 3 5 | 15 | 19 17 | 19 | 24 1 24 | 7 | 4 24 | 1 | |
| Metha-pyrilene | 3 5 | 15 | 3 3 | 7 | 24 | 10 1 24 | 10 24 | 1 4 24 | 6 |
| Psuedo-ephedrine | | 19 | 19 17 | 19 | 19 | 19 | 19 | 19 | |
| Quinine | 3 5 | 12 16 | 16 5 3 | 12 16 | 12 | 19 16 | 19 | 19 | 15 |
| Safrole | 3 5 | 15 | 7 | | | 15 | | 1 15 1 | 1 |
| Valerian | 3 5 | 1 | 6 1 2 | 1 | 24 | 4 1 | 4 1 | 2 19 | 1 |
| Cocaine | | | 3 | | 19 | 15 | 1 | | |
| Metham-phetamine | | | 3 | | 19 | 12 15 1 | 19 | | |

METHOD TO IDENTIFY CHEMICAL COMPOUNDS USING COLORIMETRIC SPOT TESTS

CROSS REFERENCE TO RELATED APPLICATIONS

This application claims the priority of U.S. provisional application No. 61/669,945 filed Jul. 10, 2012, the disclosure of which is incorporated fully by reference.

FIELD OF THE INVENTION

This invention relates generally to chemical testing, and more particularly to colorimetric spot testing.

BACKGROUND OF THE INVENTION

Many employers, law enforcement, military and even domestic consumers perform drug screening on a regular basis. Due to cost issues and ease of use, colorimetric methods are commonly used. Test reagents are reacted with suspect samples or urine, and color changes are observed. These methods are also referred to as spot or presumptive tests. Unfortunately, many of these tests are nonspecific, resulting in false positives, or if the wrong test is used, a substance abuser may go undetected. The list of pharmaceuticals and food products known to produce false positives on colorimetric tests is expansive, and the list will grow as more pharmaceuticals are introduced into the market. For example, methapyriline, the active ingredient found in some over the counter (OTC) medications, produces a false positive for stimulants. Valerian herbal tea, commonly used as a sleep aid, produces false positives for barbiturates. Employees that are subjected to urine testing are often instructed not to ingest certain OTC drugs or specific foods prior to testing. Some common tests require skilled interpretation since the results are concentration-dependent for both the reagent and sample. Thus, these so-called presumptive tests yield questionable results and require either additional colorimetric or expensive confirmatory tests.

A traditional forensic science method for identifying illegal substances entails the use of sequential spot tests to identify specific drugs. An example of a process using sequential testing is found in U.S. Pat. No. 4,104,027 for the presumptive identification of narcotics and drugs of abuse. The procedures for identifying a suspected drug entails following a series of sequential tests determined by the results of the preceding test. Examples of sequential testing procedures are found throughout the scientific literature and numerous websites.

Numerous types of drug test kits are on the market, including disposable test strips that are impregnated with specific test chemicals. Test kits that utilize disposable strips often have multiple test sites on the same strip, and each site is used to identify a specific drug class (e.g. stimulant, hallucinogen, depressant, or narcotic). Thus, a specific color change on one site may be used to identify the presence of a stimulant. The color change on a different site may be used to identify the presence of a narcotic. The technology for embedding chemicals on disposable test strips is well established for detecting the presence of illegal drugs.

SUMMARY OF THE INVENTION

A method to identify a compound of interest includes the step of subjecting a sample to a plurality of colorimetric spot tests to yield a plurality of resultant test colors. The resultant test colors are compared with reference colors to define a set of sample reference colors. Indexed reference color sets indexed for the compound of interest are provided. The indexed reference color sets are searched with one or more of the sample reference colors for a match with the set of sample reference colors. The identity of the sample as the compound of interest is then determined.

The indexed reference color set can be provided in a database. The set of reference colors can be provided on a two-dimensional surface. The set of reference colors can be provided in a database.

The colorimetric spot tests can be at least four selected from the group consisting of cobalt thiocyanate, Mecke, Marquis, Froehdes, Chen, Chromotropic Acid, $FeCl_3$, Nitric, and Simons tests. The colorimetric spot tests can comprise the cobalt thiocyanate, Mecke, Marquis, and Froehdes tests.

The method can include a step of applying color compensation to the resultant sample test colors. The color compensation can account for at least one selected from the group consisting of lighting, sample distance from light, sample distance from a sensor, sample amount, and test composition amount.

Sensing of the resultant test colors can be performed by eye or a color-sensing digital optical device. The color-sensing digital optical device can be at least one selected from the group of a digital camera and a scanner. The color-sensing digital optical device can be a mobile device camera.

At least one of the colorimetric spot tests can produce a positive indication for the compound of interest. At least one colorimetric test can produce at least two different resultant colors depending on the presence of at least two compounds of interest. The colorimetric tests can be provided on a test strip. The test strip can comprise color calibration indicia.

Between 3 to 8 different colorimetric tests can be processed in parallel. The method can further comprise the step of sensing the resultant test color of each colorimetric spot test. The method can further comprise the step of sensing at least one resultant test color as a function of time. At least one of the colorimetric spot tests can be capable of identifying a false positive for the compound of interest.

A device to identify a compound of interest can include a sensor device to sense the resultant test color of a plurality of colorimetric spot tests to provide a set of resultant sample test colors. A processor can be provided for comparing the set of resultant sample test colors with a set of predetermined reference colors to define a set of sample reference colors; for comparing the set of sample reference colors with a database of indexed reference color sets indexed for compounds of interest; searching the database of indexed reference colors for any matches; and for determining from the search the identity of the sample as a compound of interest.

The sensor can be a color-sensing digital optical device. The color-sensing digital optical device can be at least one selected from the group consisting of a digital camera and a digital scanner.

The processor can be a part of a personal computer. The sensor device and the processor can be provided in a mobile device, the mobile device comprising software for directing the processor to perform at least one of the comparing, searching and determining steps.

The device can comprise the database of indexed reference color sets. The database of indexed reference sets can be remote from the device, and the device can further comprise a wireless connection for searching the database and possibly reporting result.

The device can include a support surface for the colorimetric spot tests. The support surface can be a test strip. The device can comprise a sample platform for retaining the support surface for the colorimetric test compositions. The device can have structure for retaining the sensor a fixed distance from the sample platform. The structure can comprise a transparent window between the sensor and the sample platform. A light source can be provided for illuminating the colorimetric spot tests.

The device can have compensating structure for compensating for lighting, sample distance from light, sample distance from sensor, sample amount, and test composition amount. The compensating structure can comprises a light filter that filters selected wavelengths.

The device can further comprise structure for recording the resultant sample test color of at least one colorimetric spot test as a function of time, and wherein said processor performs the comparing and searching steps utilizing the resultant sample test color at different times. A color register and software can be provided to determine compensation for the resultant test color utilizing the color register.

A system to identify a compound of interest includes a sensor device to sense the resultant test color of each of a plurality of colorimetric spot tests to provide a set of resultant test colors. A processor is provided for comparing the set of resultant test colors with a set of predetermined reference colors to define a set of sample reference colors; for comparing the set of sample reference colors with a database of indexed reference color sets indexed for the compound of interest; and for searching the database of indexed reference colors for a match; and, for determining from the search the identity of the sample as the compound of interest. A test structure includes a base and a plurality of test sites on the base. At least one test site comprises a colorimetric testing composition for indicating the presence of the compound of interest. At least one of the colorimetric testing compositions can indicate the presence of a compound of interest and at least one of the other colorimetric testing compositions can indicate the presence of at least another compound of interest.

The sensor can be a color-sensing digital optical device. The color-sensing digital optical device can be at least one selected from the group consisting of a digital camera and a digital scanner.

The processor can be part of a personal computer. The sensor device and the processor can be provided in a mobile device. The mobile device can comprise software for directing the processor to perform at least one of the comparing, searching and determining steps.

The system can comprise a database of indexed reference color sets. The database of indexed reference sets can be remote from the device, and the device can further comprise a wireless connection for searching the database and possibly reporting result.

The test structure can be a test strip. The colorimetric spot tests can be at least four selected from the group consisting of cobalt thiocyanate, Mecke, Marquis, Froehdes, Chen, Chromotropic Acid, $FeCl_3$, Nitric, and Simons tests. The test surface can comprise from 3 to 8 colorimetric spot tests.

The system can include a sample platform for retaining the support surface for the colorimetric test compositions. Structure for retaining the sensor a fixed distance from the sample platform can be provided. The structure can include a transparent window between the sensor and the sample platform.

The system can include a light source for illuminating the colorimetric spot tests. Compensating structure for compensating for lighting, sample distance from light, sample distance from sensor, sample amount, and test composition amount can be provided. The compensating structure can comprise a light filter that filters selected wavelengths.

The system can include a structure for recording the resultant sample test color of at least one colorimetric spot test as a function of time. The processor performs the comparing and searching steps utilizing the resultant sample test color at different times. A color register and software to determine compensation for the resultant sample test color utilizing the color register can be provided.

A test structure for identifying a compound of interest includes a base and a plurality of test sites on the base. At least one test site comprises a colorimetric testing composition for indicating the presence of the compound of interest. At least one of the colorimetric testing compositions can indicate the presence of a compound of interest and at least one of the other colorimetric testing compositions can indicate the presence of at least one other compound of interest.

A kit to identify compounds of interest using simultaneous colorimetric spot tests includes at least three colorimetric spot tests. A color chart has reference colors and a color identifying indicia associated with each color on the color chart. A color logic chart has inputs for the color identifying indicia and for associating the color identifying indicia with at least the compound of interest. The colorimetric spot tests can be at least four selected from the group consisting of cobalt thiocyanate, Mecke, Marquis, Froehdes, Chen, Chromotropic Acid, $FeCl_3$, Nitric, and Simons tests.

A mobile device includes a camera to sense the resultant test color of each of a plurality of colorimetric spot tests to provide a set of resultant test colors. A processor and application software controlling the processor are provided. The application software controls the processor for comparing the set of resultant test colors with a set of predetermined reference colors to define a set of sample reference colors; for comparing the set of sample reference colors with a database of indexed reference color sets indexed for the compound of interest and possibly also false positives for the compounds of interest; and for searching the database of indexed reference colors for a match; and for determining from the search the identity of the sample as a compound of interest.

BRIEF DESCRIPTION OF THE DRAWINGS

It being understood that the invention is not limited to the arrangements and instrumentalities shown, there are shown in the drawings embodiments that are presently preferred, wherein:

FIG. 2 is an example of indexed reference color sets indexed for illicit drugs and analogs of such drugs.

FIG. 3 is an example of results for methapyrilene using four spot tests.

FIG. 4 is an example of results for chlorpromazine using four spot tests.

FIG. 5 is an example of results for safrole using four spot tests.

FIG. 6 is an example of results for 2-chloroacetophenone using four spot tests.

DETAILED DESCRIPTION OF THE INVENTION

Figure 1:
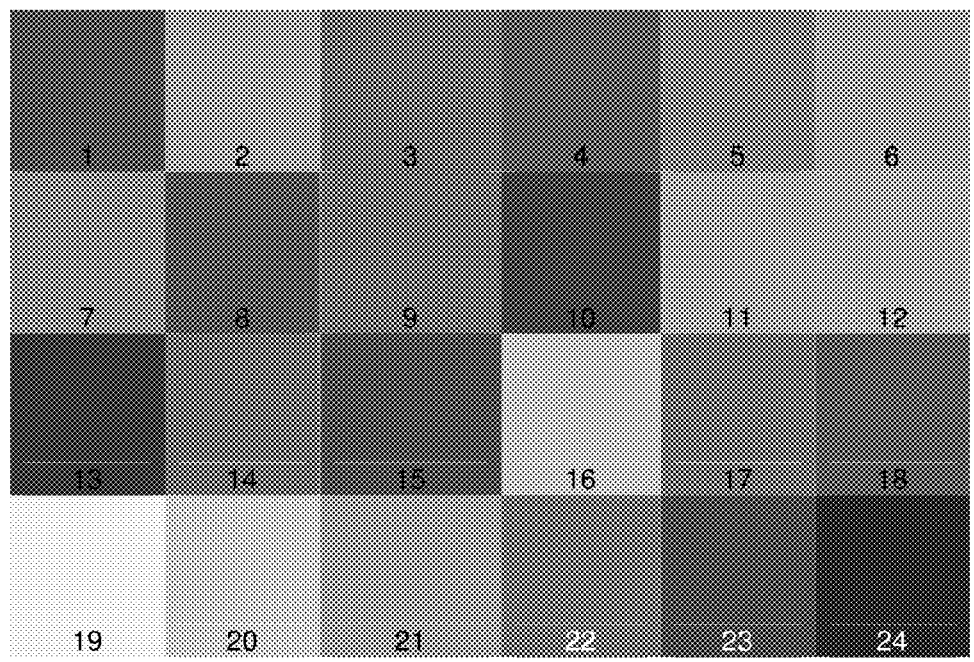
FIG. 1 is a diagram of a reference color chart.

A method to identify a compound of interest includes the step of subjecting a sample to a plurality of parallel colorimetric spot tests to yield a plurality of resultant test colors. The resultant test colors are compared with reference colors to define a set of sample reference colors. Indexed reference color sets indexed for the compound of interest are provided. The indexed reference color sets are searched with one or more of the sample reference colors for a match with the set of sample reference colors. The identity of the sample as the compound of interest is then determined.

The term colorimetric spot test as used herein refers to a chemical assay which is capable of producing a color change when contacted by a compound of interest, such that the color change or the absence of a color change when the assay is contacted with a sample provides useful information for identifying the presence or absence of the compound of interest. A plurality of such tests can be used to identify the presence or absence of many compounds of interest. The compounds of interest can be any of a wide variety of chemical compounds. In one embodiment the compound of interest comprises illicit drugs such as cocaine and methamphetamine, and can also include compounds which yield false positives for these illicit drugs. For example, methapyriline produces a false positive for stimulants while Valerian herbal tea, commonly used as a sleep aid, produces false positives for barbiturates. Examples of such illicit drug analogs are provided in Table 1.

TABLE 1

| Illicit Drug Analogs | | | |
| --- | --- | --- | --- |
| Depressant | Stimulant | Hallucinogen | Narcotic |
| Sodium glycolate | Acetominophen | Chloroacetophenone | Chlorpromazine |
| Valarian | Diphenhydramine | | Indole |
| | Methapyriline | | Quinine |
| | Pseudoephedrine | | |
| | Safrole | | |

The invention can utilize a plurality of such colorimetric spot tests to identify multiple compounds of interest in a testing procedure. Color information yielded from a plurality of such colorimetric spot tests subjected to the sample can be utilized to distinguish several compounds which might yield a positive result for a single test.

The colorimetric spot tests can in one embodiment be at least four selected from the group consisting of cobalt thiocyanate, Mecke, Marquis, Froehdes, Chen, Chromotropic Acid, FeCl$_3$, Nitric, and Simons tests. The colorimetric spot tests can comprise the cobalt thiocyanate, Mecke, Marquis, and Froehdes tests. These are colorimetric spot tests that are used for the testing of illicit drugs. Such tests are well known and described in the literature, and example formulations for such tests are summarized in Table 2:

TABLE 2

| | |
| --- | --- |
| Chen | (a) 1 mL glacial acetic acid in 100 mL distilled water |
| | (b) 1 g copper (II) sulfate in 100 mL distilled water |
| | (c) 8 g sodium hydroxide in 100 mL distilled water |
| Chromotropic | 0.1 g chromotropic acid in 100 mL sulfuric acid |
| Cobalt Thiocyanate | 2 g cobalt (II) thiocynate in 100 mL distilled water |
| FeCl$_3$ | 2 g FeCl$_3$ in 100 mL distilled water |
| Froehdes | 0.5 g sodium molybdate in 100 mL hot concentrated sulfuric acid |
| Marquis | 5 mL of 40 percent formaldehyde (v:v formaldehyde:water) in 100 mL sulfuric acid |

TABLE 2-continued

| | |
| --- | --- |
| Mecke | 1 g selenious acid in 100 mL concentrated sulfuric acid |
| Nitric | Concentrated nitric acid |
| Simon | (a) 1 g sodium nitroprusside in 50 mL distilled water, add 2 mL acetaldehyde |
| | (b) 2 g Na$_2$CO$_3$ in 100 mL distilled water |

The colorimetric spot tests when tested with a sample will yield a resultant color. These resultant test colors are used to search indexed reference color sets that have been indexed for the compound(s) of interest to identify compound(s) of interest.

Determination of the resultant test colors for purposes of searching the indexed reference color sets can be made by any suitable methodology. In one embodiment, the resultant test colors are applied to a set of reference colors to determine a set of sample reference colors. The set of reference colors can be created for this purpose or one of several standard color references can be utilized. For example, the Macbeth color chart is widely used as a color reference in the paint and electronics industries and includes a set of 24 colors that are numbered 1-24. An example of a Macbeth color chart is shown in FIG. 1. A color chart composed of 24 colors is used to identify the results of each test. The Macbeth color chart is a subset of the Munsell charts used by forensic science labs to identify color changes produced by colorimetric tests. The Macbeth chart has also been used by the film industry to calibrate true colors. Other color reference charts can be used or created for this purpose. The compounds of interest would then be indexed according to the color references that are utilized.

The resultant test colors can be compared to this chart by any suitable technique to determine a match for that colorimetric test result. A plurality of such test results will yield a set of sample reference colors.

The set of sample reference colors will then be used to search the indexed sets of reference color sets. There is shown in FIG. 2 an example of indexed sets of reference color sets. FIG. 2 is directed to illicit drugs and common compounds which are known to yield false positives for such drugs; however, the indexed sets of reference color sets can be indexed for any compounds of interest which are suited to colorimetric testing. FIG. 2 has been indexed for eight colorimetric tests commonly used to test for illicit drugs—cobalt thiocyanate, Mecke, Marquis, Froehdes, Chen, Chromotropic Acid, FeCl$_3$, Nitric, and Simons. It should be understood that the table shown in FIG. 2 could be indexed with other colorimetric tests for illicit drugs, with different combinations of such tests, or with other colorimetric tests that are suited to the particular compounds of interest, which can be many other chemical compounds that are not illicit drugs or analogs for such illicit drugs. It should be noted that different reference colors can be indexed to the same compound for the same test. The cobalt test for cocaine, for example, is indexed with 8, 18 and 3, while the Meckes test for chlorpromazine is indexed for 24, 10 and 4. Such multiple indexings account for different colors that can be produced by the same test for the same compound under differing conditions such as reactant concentration, sample concentration, time, viewing distance from the colorimetric spot test, and ambient lighting conditions.

There is shown in FIG. 2 an example of a sample which has been subjected to the cobalt thiocyanate, Mecke, Marquis, Froehdes, Chen, Chromotropic Acid, FeCl$_3$, Nitric, and Simons colorimetric tests. The resultant colors from these tests were applied to the Macbeth color chart to yield sample reference colors noted at the top of FIG. 2 according to the Macbeth numbering system: 5, 15, 17, 19, 24, 7, 4, 1, and 9. As noted, the Macbeth color reference system is used for convenience and other color references are possible.

Referring to the chart specifically for the Chen test, which is typically used in testing for the presence of amphetamines, it can be seen that the sample reference color "5" is inconclusive by itself. A "5" result from the Chen test is possible for every analog listed except diphenhydramine. Now referring to the cobalt test, the sample reference color is "17". It can be seen that such a result cannot be obtained with cocaine (8,18,3) or methamphetamine (also 8,18,3). Searching the indexed reference color sets for the sample excludes all compounds in the database except indole.

The results of the colorimetric spot tests are used together to provide useful information by processing this information in parallel. This is distinguishable from colorimetric tests which are used sequentially. For example, a sample which might produce a sample reference color 12 for the Froehdes test would be inconclusive for diphenhydramine since chlorpromazine and quinine can also yield a sample reference color 12 on the Froehdes test. Similarly a sample reference color 7 on the Marquis test is by itself inconclusive for diphenhydramine because indole can also produce a sample reference color of 7 with the Marquis test. Diphenhydramine is the only compound on the chart which can produce both a 12 on the Froehdes test and a 7 on the Marquis test, so the two test results, when processed together according to the invention, provide a conclusive result for the compounds included in the database. Such parallel processing of colorimetric test results provides significantly more information than if the tests are processed individually or sequentially.

Any number of tests can be processed according to the invention. It has been found that between 3 and 8 tests provide very acceptable results in discriminating illicit drugs from their analogs. The number of tests that are necessary will, in part, depend on the number of different compounds that reproduce identical color sets for the compound of interest. Examples were performed testing for illicit drugs and analogs thereof using 4 colorimetric tests. Four tests have been determined to readily identify an assortment of illicit drug analogs. A second and third test strip containing four additional tests each can be used to identify any true negatives or clarify any ambiguous results. It has been found that eight separate tests can be used to identify the test compounds identified in FIG. 2.

Example 1. Cobalt Thiocyanate

Figures 3, 4:
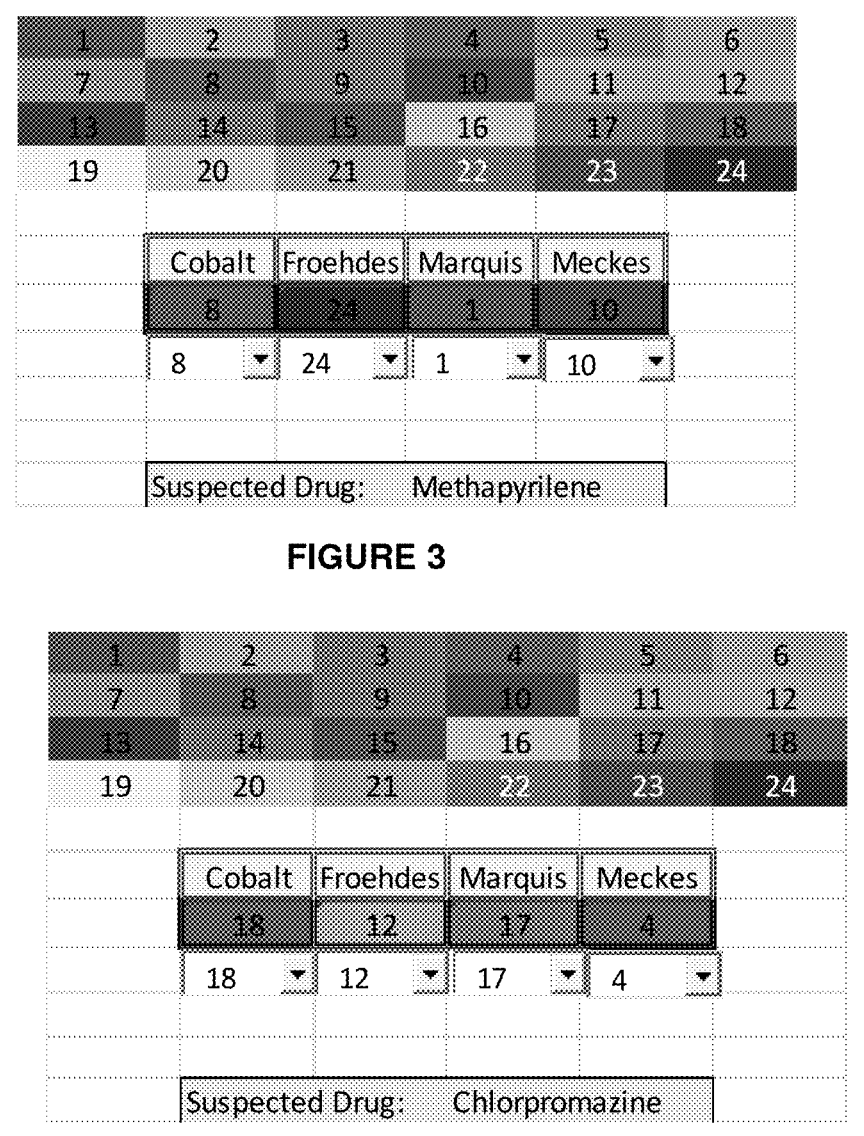

This is a standard test for the presence of cocaine and related compounds (Masoud, A. N. J. Pharm. Sci. 1975, 64, 841-844). Blue affirms the presence of such compounds, however, it is known to produce a false positive for the antihistamine, methapyrilene. Additional testing would be required to distinguish this compound from illegal substances. Simultaneous Test—the testing procedure of the invention for methapyriline would produce a signature color pattern that would readily identify this compound as an OTC drug from the reference library as shown in FIG. 3. The test result clearly discriminates methapyriline from cocaine.

Example 2. Mecke Test

This is a standard test for the presence of stimulants (Pin, T. Y.; Chin, L. S.; Hin, L. S.; Lim, L. B L AJSTD, 2010, 27, 66-75) and hallucinogens (Hasan, S.; Bromfield-Lee, D.; Oliver-Hoyo, M. T., J. A., Cintron-Maldonado, J. Chem. Ed. 2008, 85, 813-816). Positive test results produce various colors. This single test is known to produce a false positive for the antipsychotic, chlorpromazine, mistakenly indicating the presence of heroin. Simultaneous Test. The testing procedure of the invention for chlorpromazine would produce a signature color pattern that would readily identify this compound as the antipsychotic from the reference library as shown in FIG. 4.

Example 3. Marquis Test

Figures 5, 6:
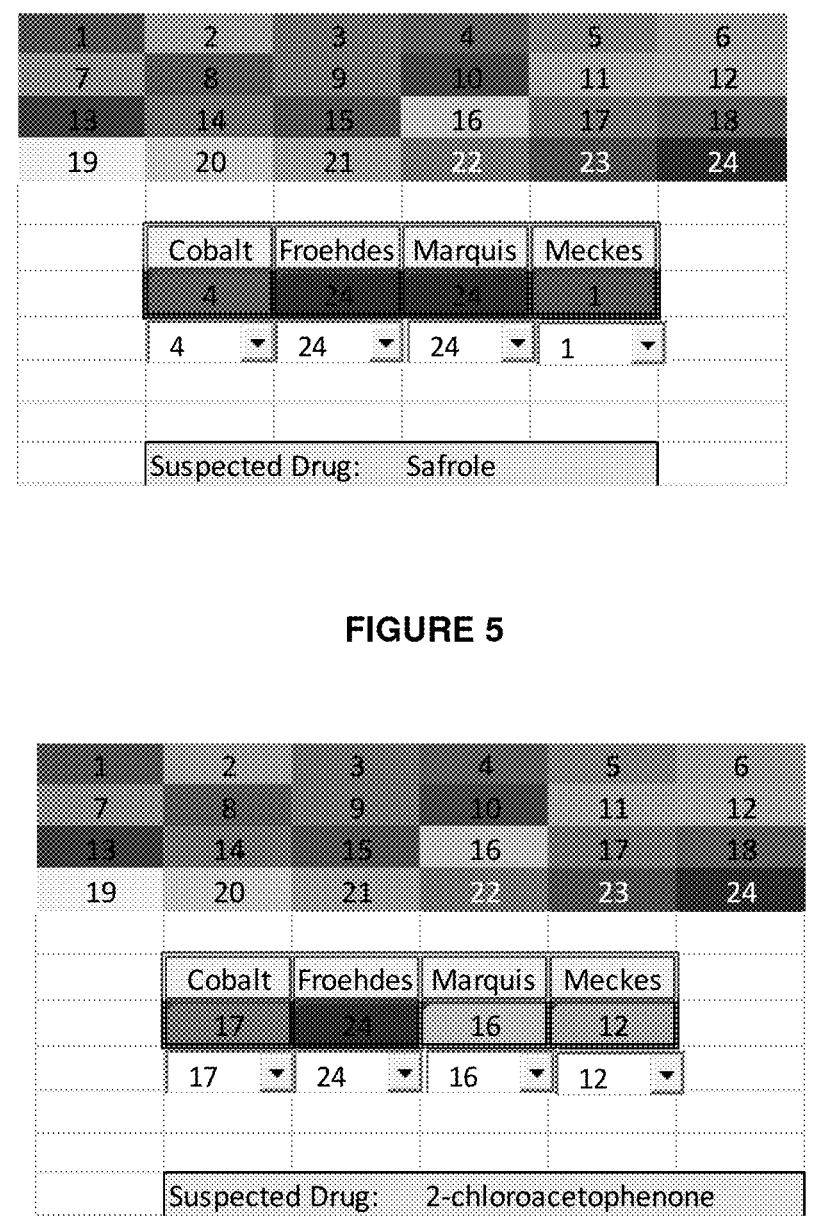

This is a standard test for that produces various colors, purple for opiates [Masoud, A. N. *J. Pharm. Sci.* 1975, 64, 841-844], other colors for stimulants and hallucinogens [O'Neal, C. L.; Crouch, D. J.; Fatah, A. A. *Forensic Sci. International,* 2000, 109, 189-201]. Although used extensively by law enforcement, the Marquis test is known to produce false positives. A naturally occurring substance in sassafras (root beer), safrole, can be mistakenly identified as a stimulant or opiate by a single test as shown in FIG. 5. Simultaneous Test—the testing procedure of the invention for safrole would produce a signature color pattern that would readily identify this compound as shown in the figure below. It is noted that safrole produces a variety of colors on different colorimetric tests, depending on concentration of safrole and test reagents, and our testing procedure takes this into account.

Example 4. Froehdes Test

Positive test results produce various colors for stimulants [Pin, T. Y.; Chin, L. S.; Hin, L. S.; Lim, L. B L *AJSTD,* 2010, 27, 66-75], hallucinogens [O'Neal, C. L.; Crouch, D. J.; Fatah, A. A. *Forensic Sci. International,* 2000, 109, 189-201], and narcotics [Lampe, K. F. J. Chem. Ed., 1958, 35, 96-97]. This is a standard test for that produces various colors, black for opiates, yellow and green for stimulants. The Froehdes test is known to produce false positives. The substance, 2-chloroacetophenone, which is used in tear gas and chemical Mace, can be mistakenly identified as an opiate by a single test, as shown in FIG. 6. Simultaneous Test—the testing procedures of the invention for 2-chloroacetophenone would produce a signature color pattern that would readily identify this compound from the reference library as shown in FIG. 6.

The set of reference colors can be provided on a two-dimensional surface such as a card or chart. The set of reference colors can be alternatively provided in a database and viewed on a monitor or mobile device screen. The indexed reference color set can also be provided in a database.

The method can include a step of applying color compensation to the resultant test colors. The color compensation can account for at least one selected from the group consisting of lighting, sample distance from light, sample distance from a sensor, sample amount, and test composition amount.

Sensing of the resultant test colors can be performed by a color-sensing digital optical device. The color-sensing digital optical device can be at least one selected from the group of a digital camera and a scanner. The color-sensing digital optical device can be a mobile device camera.

At least one of the colorimetric spot tests can produce a positive indication for both the compound of interest and at least one compound producing false positives for that compound of interest. At least one colorimetric test can produce at least two different resultant colors depending on the presence of at least two different compounds of interest. The colorimetric tests can be provided on a test strip. The test strip can comprise color calibration indicia.

The method can further comprise the step of sensing at least one resultant test color as a function of time. Certain colorimetric tests produce different colors as a function of time. This can produce a signature pattern with useful information for identifying a compound of interest. For example, methamphetamine when tested with the Froehdes test changes upon standing from colorless to orange. (Pin, T. Y.; Chin, L. S.; Hin, L. S.; Lim, L. B L *AJSTD,* 2010, 27, 66-75.) Opiates when tested with the Marquis test change color with time, as do certain analogs such as methapyrilene (Masoud, A. N. *J. Pharm. Sci.* 1975, 64, 841-844). See also Color Test Reagents/Kits for Preliminary Identification of Drugs of Abuse. NIJ Standard-0606.01, National Institutes of Justice, Washington D.C., 2000.

Figure 7:
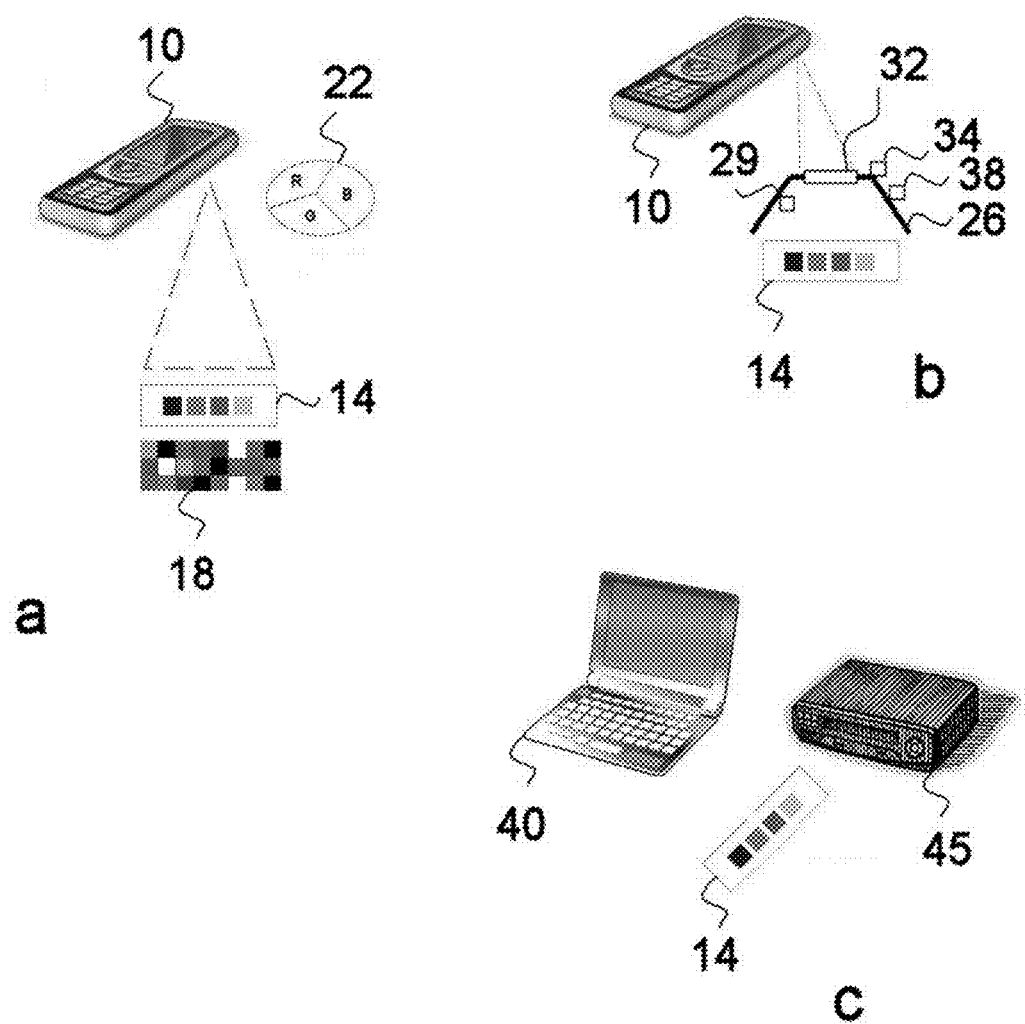
FIG. 7a-c is a schematic diagram of a device and system for testing for compounds of interest using colorimetric spot tests.

A device to identify a compound of interest includes a sensor device to sense the resultant test color of a plurality of colorimetric spot tests to provide a set of resultant test colors. A processor can be provided for comparing the set of resultant test colors with a set of predetermined reference colors to define a set of sample reference colors; for comparing the set of sample reference colors with a database of indexed reference color sets indexed for compounds of interest; and for searching the database of indexed reference colors for a match; and for determining from the search the identity of the sample as a compound of interest. Such a device can be in a mobile device as shown in FIG. 7, or in a dedicated device.

The sensor can be a color-sensing digital optical device. The color-sensing digital optical device can be at least one selected from the group consisting of a digital camera and a digital scanner.

The processor can be a part of a personal computer. The sensor device and the processor can be provided in a mobile device, the mobile device comprising software for directing the processor to perform at least one of the comparing, searching and determining steps.

The device can comprise the database of indexed reference color sets. The database of indexed reference sets can be remote from the device, and the device can further comprise a wireless connection for searching the database and possibly also reporting results.

The device can include a support surface for the colorimetric spot tests. The support surface can be a test strip. The device can comprise a sample platform for retaining the support surface for the colorimetric test compositions. The device can have structure for retaining the sensor a fixed distance from the sample platform. The structure can comprise a transparent window between the sensor and the sample platform. A light source can be provided for illuminating the colorimetric spot tests.

The device can have compensating structure for compensating for lighting, sample distance from light, sample distance from sensor, sample amount, and test composition amount. The compensating structure can comprise of a light filter that filters selected wavelengths.

The device can further comprise structure for recording the resultant sample test color of at least one colorimetric spot test as a function of time, and wherein said processor performs the comparing and searching steps utilizing the resultant sample test color at different times. A color register and software can be provided to determine compensation for the resultant test color utilizing the color register.

A system to identify a compound of interest includes a sensor device to sense the resultant test color of each of a plurality of colorimetric spot tests to provide a set of resultant test colors. A processor is provided for comparing the set of resultant sample test colors with a set of predetermined reference colors to define a set of sample reference colors; for comparing the set of sample reference colors with a database of indexed reference color sets indexed for the compound of interest; and for searching the database of indexed reference colors for a match; and, for determining from the search the identity of the sample as the compound of interest. A test structure includes a base and a plurality of test sites on the base. At least one test site comprises a colorimetric testing composition for indicating the presence of the compound of interest. At least one of the colorimetric testing compositions can indicate the presence of a compound of interest.

Such a system is shown in FIG. 7*a-c*. A mobile device 10 with a camera is used to take an image of a test strip 14 according to the invention, as shown in FIG. 7*a*. A set of reference colors such as Macbeth chart 18 can be utilized to color-calibrate the camera in the mobile device 10. A filter for selected wavelengths of light can be provided such as red breen blue (RGB) filter 22. There is shown in FIG. 7*b* a device for assisting in the sensing of resultant test colors from the test strip 14. The device includes a housing 26 having a window 32 for permitting the camera from the mobile device to record a picture of the test strip 14. A light source 29 can be provided to illuminate the test strip 14. The window 32 could be replaced with a built-in camera. A processor 34 can be provided to control the process including the lighting 29 and possible camera 32. A wireless transmitter 38 can be provided to access a database or remote processor and/or to communicate results wirelessly. There is shown in FIG. 7*c* a test strip 14 that can be placed into a reader or scanner 45 and the results communicated to a processor such as laptop 40. The sensor can be a color-sensing digital optical device. The color-sensing digital optical device can be at least one selected from the group consisting of a digital camera and a digital scanner.

The processor can be part of a personal computer. The sensor device and the processor can be provided in a mobile device. The mobile device can comprise software for directing the processor to perform at least one of the comparing, searching and determining steps.

The system can comprise a database of indexed reference color sets. The database of indexed reference sets can be remote from the device, and the device can further comprise a wireless connection for searching the database.

The test structure can be a test strip. The colorimetric spot tests can be at least four selected from the group consisting of cobalt thiocyanate, Mecke, Marquis, Froehdes, Chen, Chromotropic Acid, FeCl$_3$, Nitric, and Simons tests. The test surface can comprise from 3 to 8 colorimetric spot tests.

The system can include a sample platform for retaining the support surface for the colorimetric test compositions. Structure for retaining the sensor a fixed distance from the sample platform can be provided. The structure can include a transparent window between the sensor and the sample platform.

The system can include a light source for illuminating the colorimetric spot tests. Compensating structure for compensating for lighting, sample distance from light, sample distance from sensor, sample amount, and test composition amount can be provided. The compensating structure can comprise of a light filter to filter selected wavelengths.

The system can include structure for recording the resultant test color of at least one colorimetric spot test as a function of time. The processor performs the comparing and searching steps utilizing the resultant sample test color at different times. A color register and software to determine compensation for the resultant sample test color utilizing the color register can be provided.

A test structure for identifying a compound of interest includes a base and a plurality of test sites on the base. At least one test site comprises a colorimetric testing composition for indicating the presence of the compound of interest. At least one of the colorimetric testing compositions can indicate the presence of a compound of interest and at least one of the other colorimetric testing compositions can indicate the presence of at least one other compound of interest. At least one colorimetric testing composition can produce at least two different resultant colors depending on the presence of at least two compounds of interest.

A kit to identify sample analogs of illicit chemical compounds using simultaneous colorimetric spot tests includes at least three colorimetric spot tests. A color chart has reference colors and a color identifying indicia associated with each color on the color chart. A color logic chart has inputs for the color identifying indicia and for associating the color identifying indicia with at least one compound of interest. The colorimetric spot tests can be at least four selected from the group consisting of cobalt thiocyanate, Mecke, Marquis, Froehdes, Chen, Chromotropic Acid, $FeCl_3$, Nitric, and Simons tests.

A mobile device includes a camera to sense the resultant test color of each of a plurality of colorimetric spot tests to provide a set of resultant test colors. The mobile device can be a phone, tablet, laptop or other mobile device. A processor and application software controlling the processor are provided. The application software controls the processor for comparing the set of resultant sample test colors with a set of predetermined reference colors to define a set of sample reference colors; comparing the set of sample reference colors with a database of indexed reference color sets indexed for the compound of interest; and for searching the database of indexed reference colors for a match; and, for determining from the search, the identity of the sample as a compound of interest.

This invention can be embodied in other forms without departing from the spirit or essential attributes thereof. Modifications and variations of the methods and systems disclosed herein are possible. All references noted in this application are hereby fully incorporated by reference.

I claim:

1. A method to identify a compound of interest as an illicit drug with a mobile device having a color camera, comprising the steps of:
   providing a portable sample platform having thereon a set of different colorimetric test sites for a set of different colorimetric tests;
   placing sample portions of the compound of interest on each of the set of test sites;
   subjecting the sample portions to the set of different colorimetric tests at the set of colorimetric test sites to yield a set of different resultant test colors;
   simultaneously sensing the set of different resultant test colors with the camera for all of the colorimetric test sites on the sample platform to produce a set of sensed colors for the different colorimetric tests;
   communicating the set of sensed colors to a processor;
   providing a database comprising a set comprising a plurality of reference colors for each of the different colorimetric tests of the set of different colorimetric tests, and color comparison reference results for the illicit drug for the set of different colorimetric tests;
   the processor comparing the set of sensed colors with the set of reference colors for each of the different colorimetric tests to produce a set of different colorimetric test comparison results;
   the processor analyzing and processing in parallel the set of different colorimetric test comparison results and the color comparison reference results for an illicit drug whether the compound of interest is an illicit drug and to screen for false positives from the colorimetric tests.

2. The method of claim 1, wherein the colorimetric tests are at least four selected from the group consisting of cobalt thiocyanate, Mecke, Marquis, Froehdes, Chen, Chromotropic Acid, $FeCl_3$, Nitric, and Simons tests.

3. The method of claim 1, wherein the colorimetric tests comprise the cobalt thiocyanate, Mecke, Marquis, and Froehdes tests.

4. The method of claim 1, further comprising the step of applying color compensation to the resultant test colors.

5. The method of claim 4, wherein the color compensation compensates for at least one selected from the group consisting of lighting, sample distance from light, sample distance from sensor, sample amount, and test composition amount.

6. The method of claim 1, wherein at least one of the colorimetric tests produces a positive indication for both the illicit drug and at least one compound producing false positives for that compound of interest.

7. The method of claim 1, wherein at least one colorimetric test produces at least two different resultant test colors depending on the presence of at least two compounds of interest.

8. The method of claim 1, wherein the colorimetric tests are provided on a test strip.

9. The method of claim 8, wherein the test strip comprises color calibration indicia.

10. The method of claim 1, further defining 3 to 8 different colorimetric tests are performed simultaneously.

11. The method of claim 1, further comprising the step of sensing at least one resultant test color as a function of time.

12. The method of claim 1, wherein at least one of the colorimetric tests is capable of identifying a false positive for the illicit drug.

* * * * *